US012324891B2

(12) United States Patent
Cameron

(10) Patent No.: US 12,324,891 B2
(45) Date of Patent: Jun. 10, 2025

(54) SUPPOSITORY APPLICATOR

(71) Applicant: Neville Cameron, Grayson, GA (US)

(72) Inventor: Neville Cameron, Grayson, GA (US)

( * ) Notice: Subject to any disclaimer, the term of this patent is extended or adjusted under 35 U.S.C. 154(b) by 795 days.

(21) Appl. No.: 17/666,655

(22) Filed: Feb. 8, 2022

(65) Prior Publication Data
US 2022/0265977 A1 Aug. 25, 2022

Related U.S. Application Data

(60) Provisional application No. 63/152,931, filed on Feb. 24, 2021.

(51) Int. Cl.
*A61M 31/00* (2006.01)
*A61M 3/02* (2006.01)

(52) U.S. Cl.
CPC ........ *A61M 31/007* (2013.01); *A61M 3/0233* (2013.01); *A61M 3/0258* (2013.01); *A61M 3/0262* (2013.01); *A61M 3/0279* (2013.01); *A61M 31/00* (2013.01); *A61M 31/002* (2013.01); *A61M 2210/1064* (2013.01); *A61M 2210/1067* (2013.01)

(58) Field of Classification Search
CPC .. A61M 31/007; A61M 31/002; A61M 31/00; A61M 3/0262; A61M 3/0233; A61M 3/0258; A61M 3/0279; A61M 2210/1067; A61M 2210/1064
See application file for complete search history.

(56) References Cited

U.S. PATENT DOCUMENTS

2005/0043706 A1\* 2/2005 Eaton ..................... A61K 31/58
604/500
2009/0281483 A1\* 11/2009 Baker ................. A61M 3/0212
604/35

\* cited by examiner

*Primary Examiner* — Tasnim Mehjabin Ahmed
(74) *Attorney, Agent, or Firm* — Asgaard Patent Services, LLC; F. Wayne Thompson, Jr.

(57) ABSTRACT

Disclosed are implementations of a suppository applicator configured for use in depositing a suppository product in a body cavity, such as the rectum. An example suppository applicator comprises a handle connected to a tool head by an elongate shaft, and a disposable applicator removably attached to the tool head. The disposable applicator is configured to contain a suppository product therein. The suppository applicator is configured such that rotation of the handle causes the suppository product to be expelled from the disposable applicator. Also disclosed are implementations of an enema dispenser. An example apparatus comprises a handle connected to a tool head by an elongate shaft, and a driving mechanism. The tool head includes an enema dispenser comprising a bottle holder, a piston, and a bottle configured to contain an enema liquid. The driving mechanism is configured to cause the piston to compress the bottle of the enema dispenser when actuated, thereby dispensing a volume of liquid contained in the bottle.

18 Claims, 9 Drawing Sheets

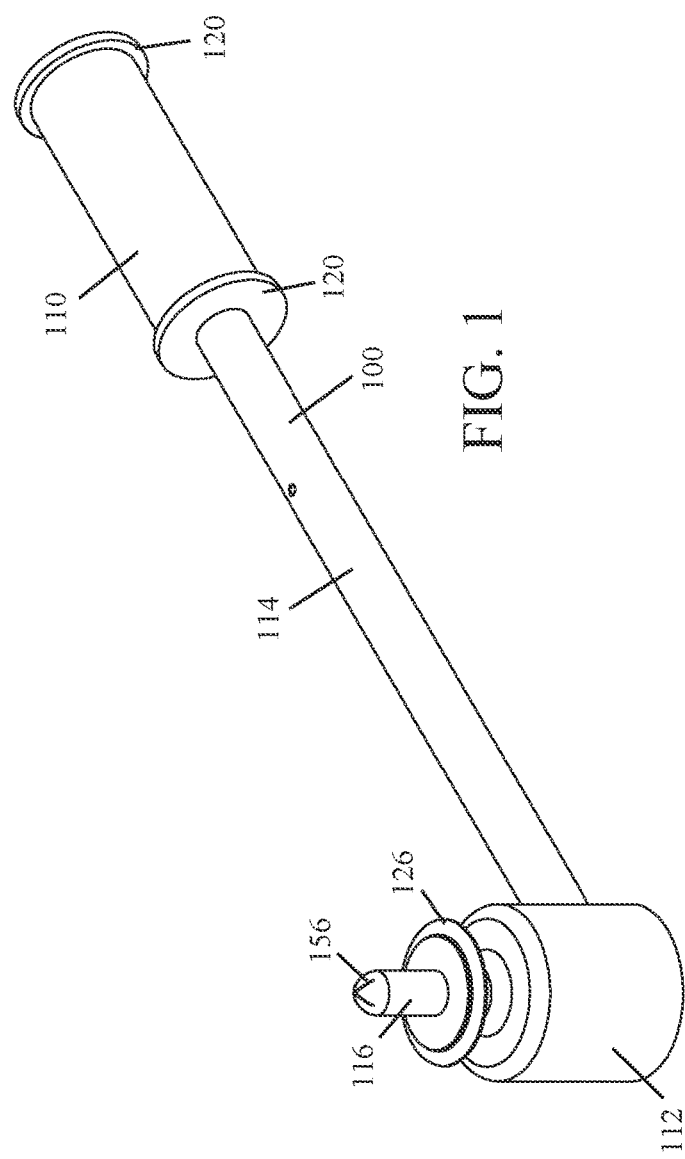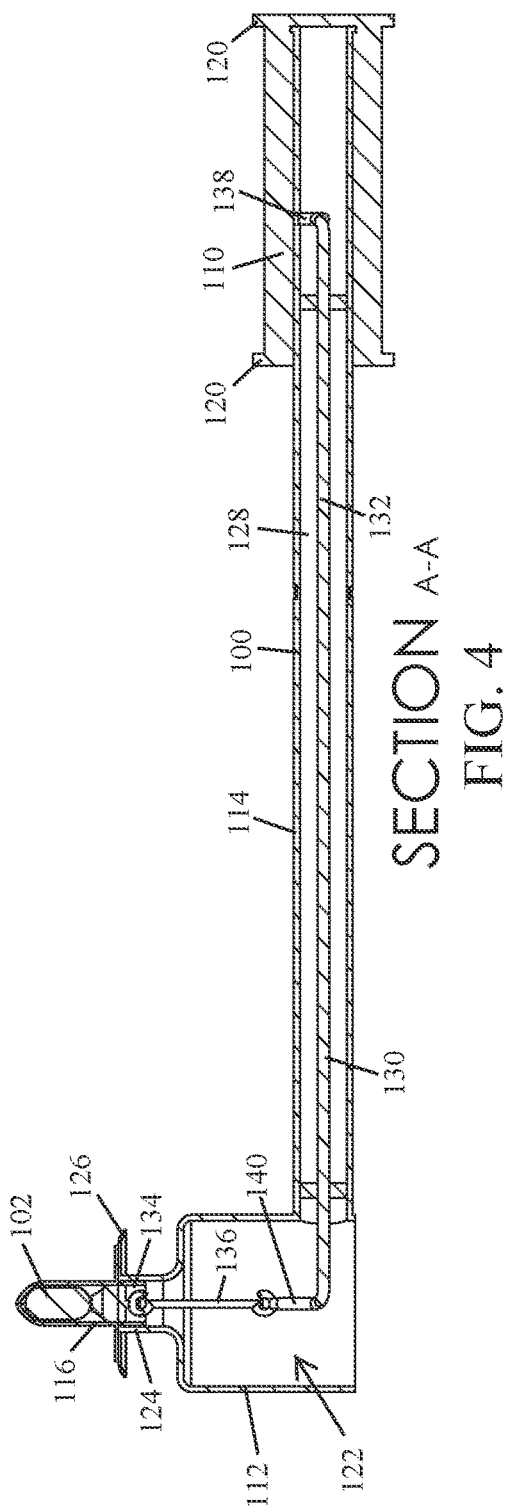

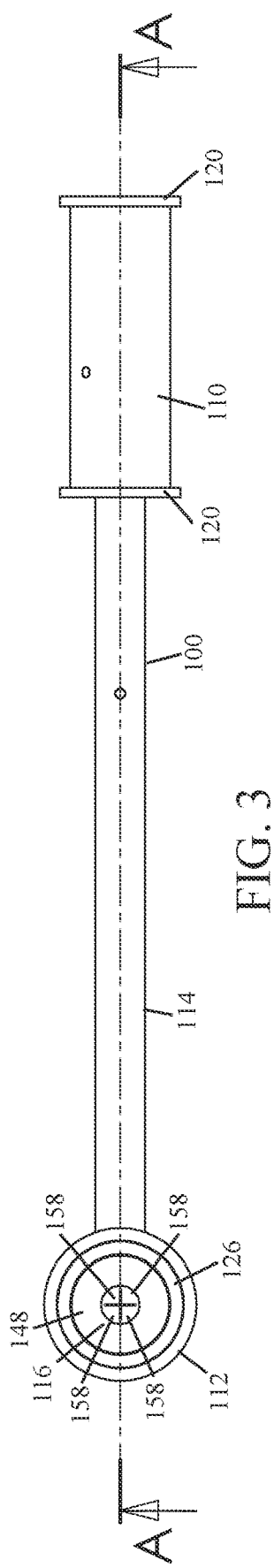
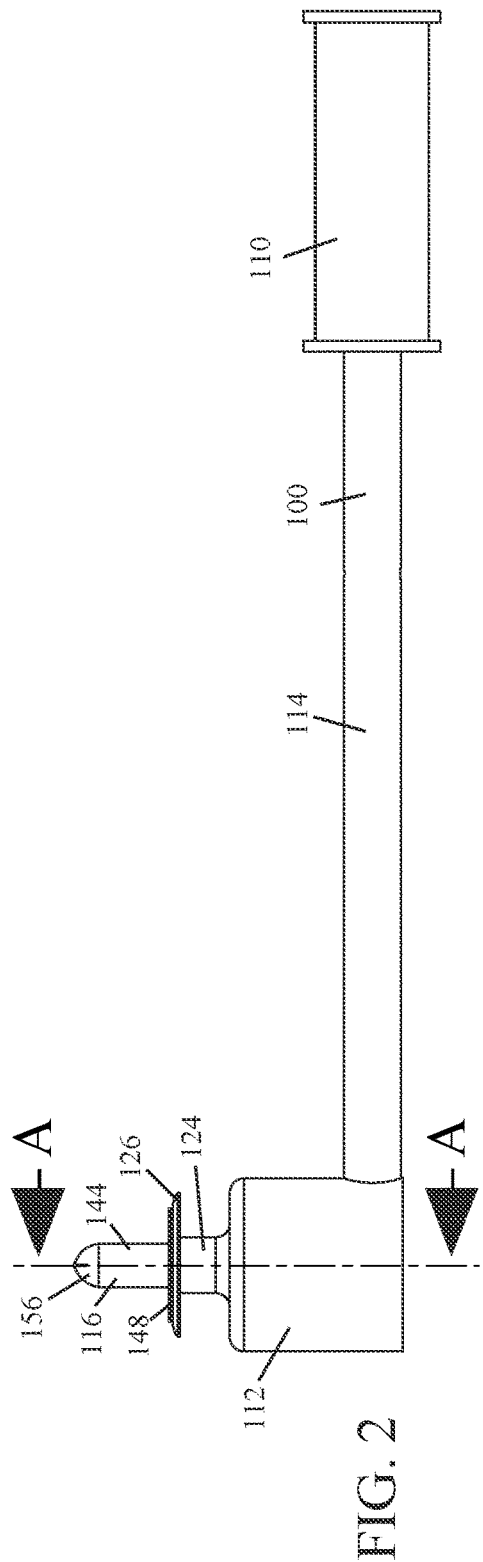
FIG. 3
FIG. 2

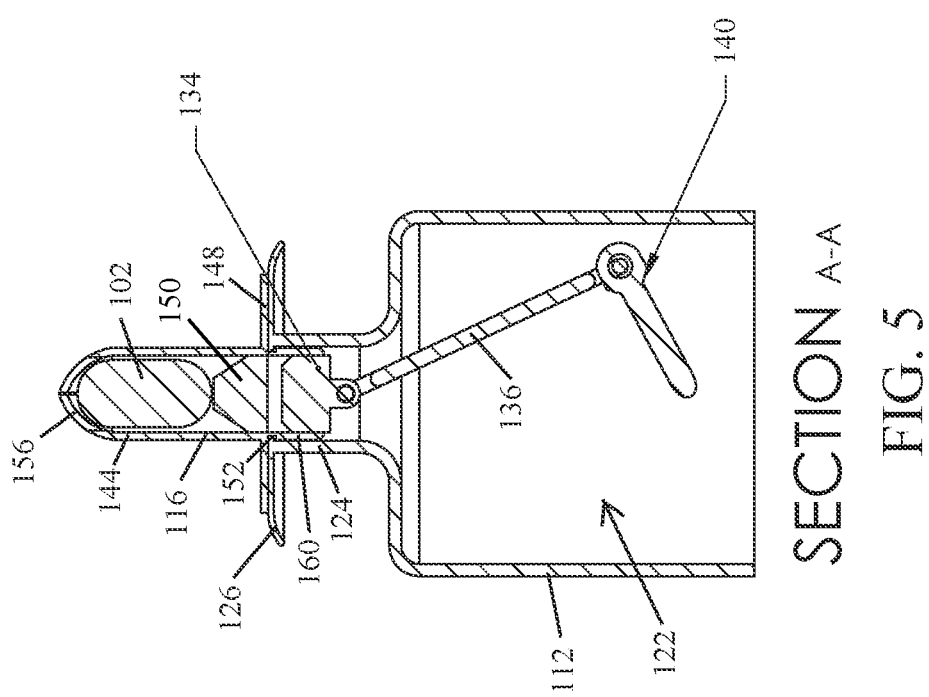

SECTION L-L

DETAIL B

SECTION A-A

SECTION A-A

SUPPOSITORY APPLICATOR

CROSS REFERENCE TO RELATED APPLICATION

This application claims the benefit of U.S. Provisional Application Ser. No. 63/152,931, filed on Feb. 24, 2021, the entirety of which is incorporated herein by reference.

TECHNICAL FIELD

This disclosure relates to implementations of a suppository applicator. In particular, the present invention is directed to an applicator for the rectal insertion of suppositories.

BACKGROUND

Various methods exist for dispensing medication to a patient. When insertion into a body cavity is desired, manual applicators to assist with the insertion of a suppository into a body cavity are utilized because they provide a safe, reliable, and hygienic means for controlling the insertion of a suppository. Most applicators incorporate a plunger slidingly disposed in a longitudinal bore such that axial movement of the plunger causes a suppository to exit the longitudinal bore through an exit port.

With a spinal cord injury, damage can occur to the nerves that allows a person to control bowel movements. If the spinal injury occurs at or above the twelfth thoracic vertebra (i.e., the T-12 vertebrae) in the spine, the ability to feel when the rectum is full may be lost. In this case, the bowel will empty by reflex in response to the rectum filling up with stool. Further, those with spinal injuries at or above the T-12 vertebrae have impaired mobility, often being wheelchair bound. Even still, these individuals would be capable of using the commode without assistance if provided with a suitably configured chair and suppository applicator (or enema dispenser).

Accordingly, it can be seen that needs exist for the suppository applicator disclosed herein. It is to the provision of a suppository applicator configured to address these needs, and others, that the present invention is primarily directed.

SUMMARY OF THE INVENTION

It is to be understood that this summary is not an extensive overview of the disclosure. This summary is exemplary and not restrictive, and it is intended neither to identify key or critical elements of the disclosure nor delineate the scope thereof. The sole purpose of this summary is to explain and exemplify certain concepts of the disclosure as an introduction to the following complete and extensive detailed description.

Disclosed are implementations of a suppository applicator configured for use in depositing a suppository product in a body cavity, such as the rectum. An example suppository applicator comprises a handle connected to a tool head by an elongate shaft, and a disposable applicator removably attached to the tool head. The disposable applicator is configured (i.e., sized and shaped) to contain a suppository product therein. The suppository applicator is configured such that rotation of the handle causes the suppository product to be expelled from the disposable applicator.

Another example suppository applicator comprises a handle connected to a tool head by an elongate shaft, a disposable applicator removably attached to the tool head, and a driving mechanism. The disposable applicator is configured to contain the suppository product and the driving mechanism is configured to expel the suppository product from the disposable applicator when actuated.

Also disclosed are implementations of an enema dispenser. An example apparatus comprises a handle connected to a tool head by an elongate shaft, and a driving mechanism. The tool head includes an enema dispenser comprising a bottle holder, a piston, and a bottle configured to contain an enema liquid. The driving mechanism is configured to cause the piston to compress the bottle of the enema dispenser when actuated. In this way, a volume of liquid contained in the bottle is dispensed.

BRIEF DESCRIPTION OF THE DRAWINGS

FIG. 1 illustrates an isometric view of an example suppository applicator according to the principles of the present disclosure.

FIG. 2 illustrates a side view of the suppository applicator shown in FIG. 1.

FIG. 3 illustrates a top plan view of the suppository applicator shown in FIG. 1.

FIG. 4 illustrates a side cutaway view of the suppository taken along line A-A shown in FIG. 3.

FIG. 5 illustrates a cutaway view of the tool head taken along line A-A shown in FIG. 2.

Like reference numerals refer to corresponding parts throughout the several views of the drawings.

DETAILED DESCRIPTION

Figure 6:
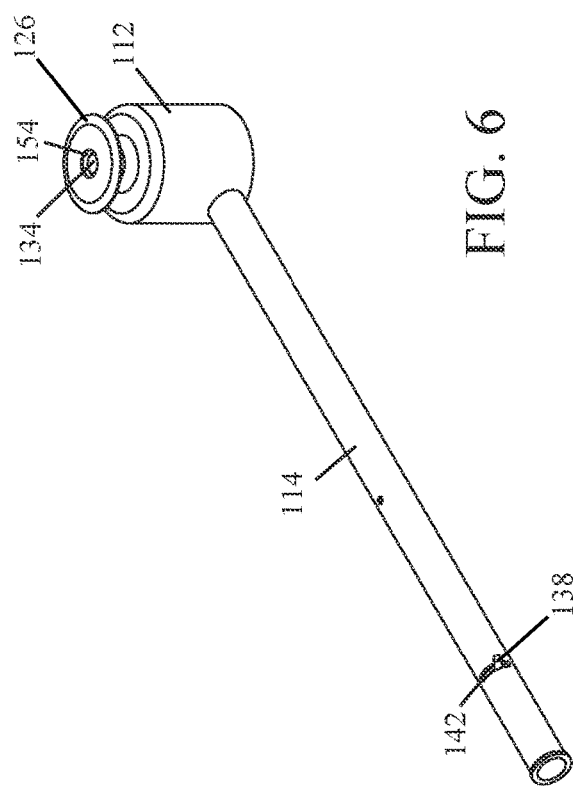
FIGS. 6 and 7 illustrate the suppository applicator shown in FIG. 1 without the handle on the elongate shaft or the disposable applicator attached to the tool head.
Figure 7:
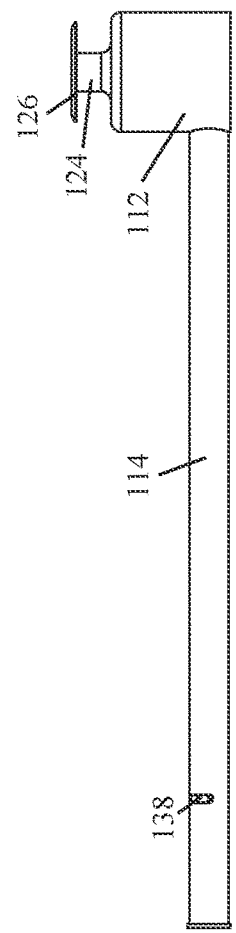

FIGS. 1-4 illustrate an example suppository applicator 100 according to the principles of the present disclosure. The suppository applicator 100 is configured for use in depositing a suppository product 102 in a body cavity, such as the rectum. The suppository applicator 100 comprising: a handle 110 connected to a tool head 112 by an elongate shaft 114; and a disposable applicator 116 removably attached to the tool head 112. The disposable applicator 116 is configured (i.e., sized and shaped) to contain a suppository product 102 therein. The suppository applicator 100 is configured so that rotation of the handle 110 causes the suppository product 102 to be expelled from the disposable applicator 116 (see, e.g., FIGS. 4 and 5).

As shown in FIGS. 1-7, the elongate shaft 114 of the suppository applicator 100 is a cylindrical tube. The handle 110 is positioned about an end of the elongate shaft 114 and configured to be grasp and rotated by a human hand. The handle 110 has a generally cylindrical shape and includes an annual flange 120 on each end thereof. The tool head 112 is attached to another end of the elongate shaft 114, opposite the handle 110. The tool head 112 defines an internal cavity 122 and includes a tubular neck portion 124 that has an annular flange 126 on one end.

As shown best in FIGS. 4 and 5, the suppository applicator 100 further comprises a driving mechanism 130 configured to expel the suppository product 102 from the disposable applicator 116 when the handle 110 is rotated about the elongate shaft 114 of the suppository applicator 100. The driving mechanism 130 comprising a crankshaft 132, a drive pin 134, and a connecting rod 136. The crankshaft 132 extends through a longitudinally extending opening 128 of the elongate shaft 114 into the internal cavity 122 of the tool head 112. The crankshaft 132 includes a crank 138, 140 on each end, one crank extends 138 through a slot 142 in the handle end of the elongate shaft 114 (see, e.g., FIG. 6) and the other crank 140 is located within the cavity 122 of the tool head 112. The first crank 138 is operably connected to the handle 110 and the second crank 140 is operably connected to the drive pin 134 via the connecting rod 136. The slot 142 in the handle end of the elongate shaft 114 is configured to limit rotation of the first crank 138 and thereby the handle 110. Rotation of the handle 110 causes the drive pin 134 to reciprocate within an opening 154 defined by the tubular neck portion 124 of the tool head 112 (see, e.g., FIG. 6).

In other implementations, instead of the handle 110, an electric motor with a direct-drive mechanism, or other device(s), could be used to actuate the driving mechanism 130 (i.e., cause the crankshaft 132 to rotate). In such an implementation, the handle 110 may include a button to actuate the electric motor and thereby the driving mechanism 130 of the suppository actuator 100.

Figure 8:
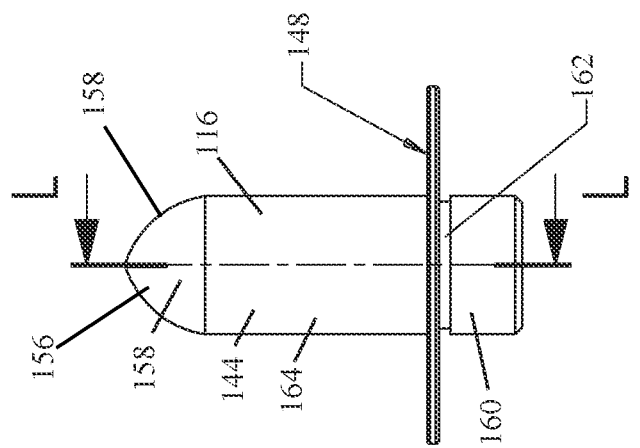
FIG. 8 illustrates a side view of the disposable applicator shown in FIG. 1.
Figure 9:
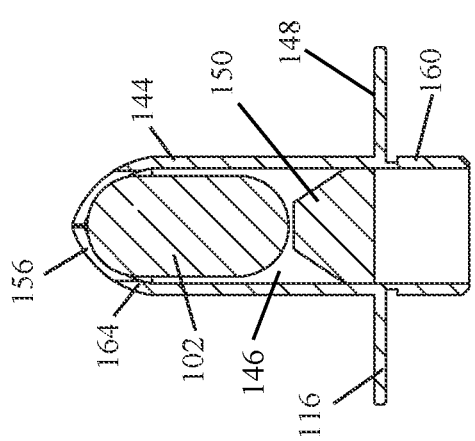
FIG. 9 illustrates a side cutaway view of the disposable applicator taken along line L-L shown in FIG. 8.
Figure 12:
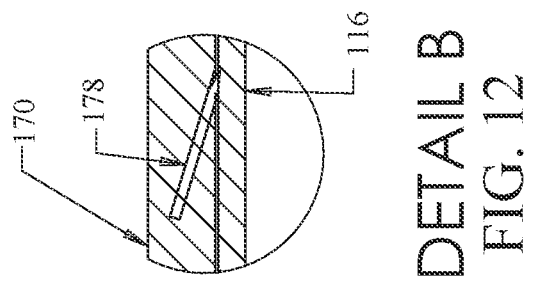
FIG. 12 illustrates an enlarged view of a portion of the suppository tool shown in FIG. 11, wherein an example barb is shown.
Figure 13:
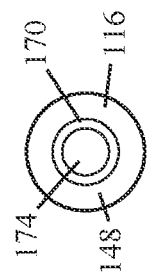
FIG. 13 illustrates a top plan view of the suppository tool shown in FIG. 10.
Figure 11:
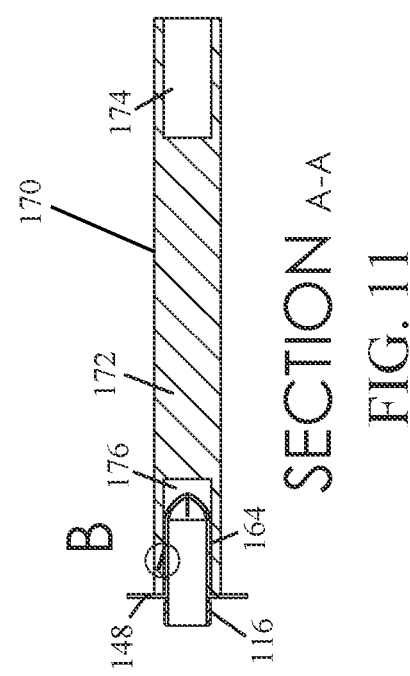
FIG. 11 illustrates a side cutaway view of the suppository tool taken along line A-A shown in FIG. 10.
Figure 10:
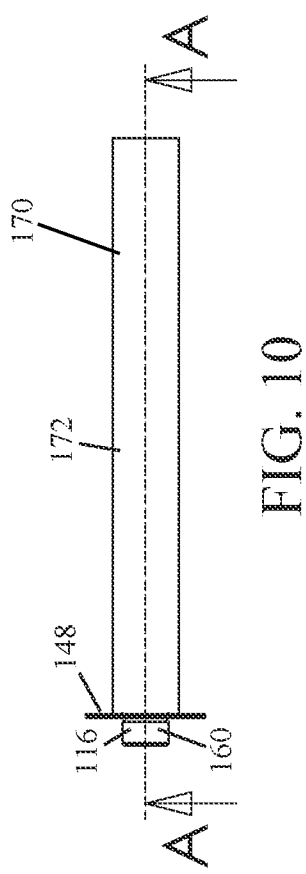
FIG. 10 illustrates a side view of an example suppository tool according to the principles of the present disclosure.

As shown best in FIGS. 8 and 9, the disposable applicator 116 comprises a barrel member 144 formed with a longitudinal bore 146, and a disc shaped guard 148 positioned along the length of and perpendicular to the barrel member 144. The longitudinal bore 146 extends through the barrel member 144 of the disposable applicator 116. The disc shaped guard 148 prevents the barrel member 144 from being over inserted into a body cavity, such as the rectum. The barrel member 144 also includes an insertion tip 156, formed as one-piece with the barrel member 144, that is dome-shaped to facilitate insertion of the barrel member 144 into a rectal cavity. The insertion tip 156 is made of a thin, flexible material and has a plurality of soft, flexible petals 158 arranged to form the dome-shape. The petals 158 are capable of radially flexing (i.e., bending outward) to provide an opening through which the suppository product 102 can exit when it is pushed forward by a piston 150. The piston 150 is slidably disposed in the longitudinal bore 146 such that relative axial movement of the piston 150 in the longitudinal bore 146 causes a suppository product 102 to exit through the insertion tip 156 of the disposable applicator 116.

Although not shown in the drawings, in some implementations, the disposable applicator 116 may not include a piston 150 and instead use a plastic film to seal the suppository product 102 within the longitudinal bore 146 of the barrel member 144. In such an implementation, the drive pin 134 would be configured to rupture the plastic film and push the suppository product 102 through the insertion tip 156 of the disposable applicator 116.

As shown best in FIG. 5, a proximal section 160 of the disposable applicator 116 is configured to fit within the opening 154 defined by the tubular neck portion 124 of the tool head 112. The proximal section 160 extends from an end of the disposable applicator 116 to the disc shaped guard member 148 of the disposable applicator 116 (see, e.g., FIG. 9). The proximal section 160 of the disposable applicator 116 includes a circumferential groove 162 configured to receive a corresponding ridge 152 found in the opening 154 defined by the tubular neck portion 124 of the tool head 112. In this way, the disposable applicator 116 can be removably attached to the tool head 112 of the suppository applicator 100.

Although not shown in the drawings, it should be understood that an adhesive could be used to removably secure the disposable applicator 116 to the tool head 112 of the suppository applicator 100. Such an implementation may not include the circumferential groove 162 on the proximal section 160 of the disposable applicator 116 or the corresponding ridge 152 found in the opening 154 of the tool head 112.

In some implementations, a suppository tool 170 may be used to install a disposable applicator 116 onto the tool head 112 of the suppository applicator 100. The suppository tool 170 can also be used to remove a disposable applicator 116 from the tool head 112.

As shown in FIGS. 10-13, the suppository tool 170 comprises a cylindrical, elongate body 172 that has an opening, 174, 176 in each end thereof. Each opening 174, 176 is configured to receive a distal section 164 of a disposable applicator 116. The distal section 164 of a disposable applicator 116 extends from the disc shaped guard member 148 to the end of the insertion tip 156. In some implementation, the opening 176 used to remove a disposable applicator 116 from the tool head 112 of a suppository applicator 100 includes a barb 178 therein. The barb 178 is at an angel relative to the longitudinal axis of the opening 176 and positioned to catch on the distal section 164 of a disposable applicator 116. In this way, the suppository tool 170 can be used to remove the disposable applicator 116 from the tool head 112 of the suppository applicator 100.

The following steps may be used to install a disposable applicator 116 onto the tool head 112 of a suppository applicator 100. Initially, the distal section 164 of a disposable applicator 116 is inserted into the opening 174 in a first end of the suppository tool 170. Then, the suppository tool 170 is used to insert the proximal section 160 of the disposable applicator 116 into the opening 154 defined by the tubular neck portion 124 of the tool head 112. The circumferential groove 162 of the disposable applicator 116 will engage with the corresponding ridge 152 in the opening 154 of the tool head 112. Next, the suppository tool 170 will be withdrawn from the distal section 164 of the disposable applicator 116, leaving it affixed to the tool head 112 of the suppository applicator 100.

The following steps may be used to remove a disposable applicator 116 from the tool head 112 of a suppository applicator 100. Initially, the distal section 164 of the disposable applicator 116 is inserted into the opening 176 in a second end of the suppository tool 170. This allows the barb 178 therein to engage with (i.e., stick into) the distal section 164 of the disposable applicator 116. Then, the suppository tool 170 is used to withdraw the proximal section 160 of the disposable applicator 116 from the opening 154 defined by the tubular neck portion 124 of the tool head 112. In this way, the disposable applicator 116 can be removed from the tool head 112 and discarded after use.

In some implementations, a suppository applicator 100 may be configured for use as an enema. Such an implementation of the suppository applicator 100 would have a modified tool head 112 that includes an enema dispenser 200 used to inject fluid into a body cavity, such as the rectum.

Figure 15:
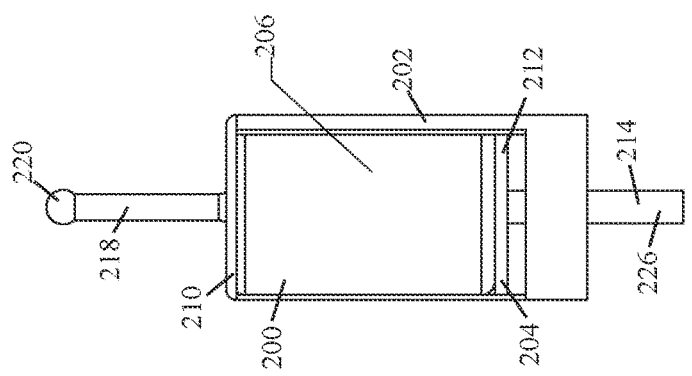
FIGS. 14 and 15 illustrate an example enema dispenser according to the principles of the present disclosure.
Figure 14:
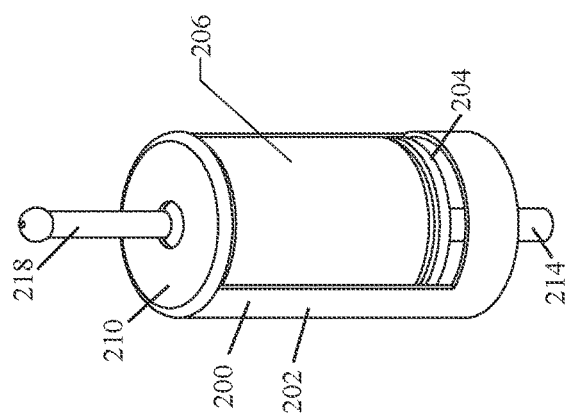

As shown in FIGS. 14 and 15, an example enema dispenser 200 may comprise a bottle holder 202, a piston 204, and a bottle 206 configured to contain an enema liquid.

Figure 16:
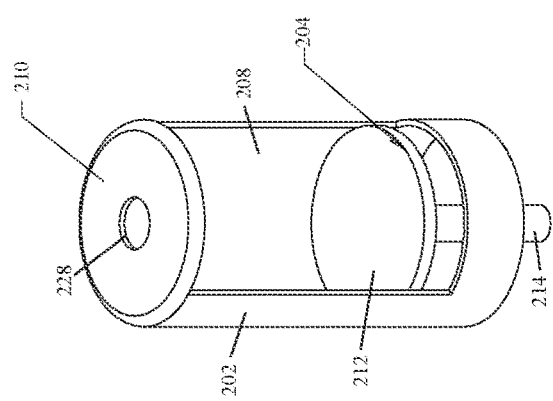
FIGS. 16 and 17 illustrate the enema dispenser shown in FIGS. 14 and 15 without the bottle positioned in the bottle holder.
Figure 17:
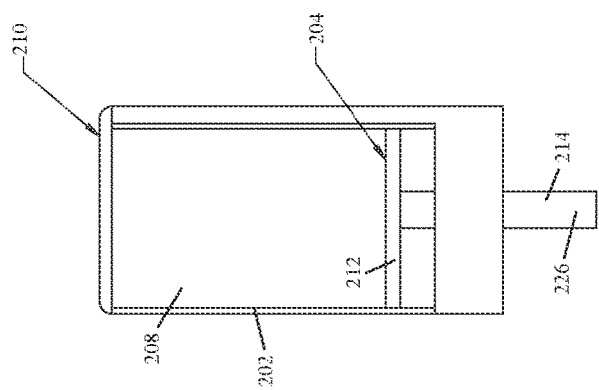

As shown best in FIGS. 16 and 17, the bottle holder 202 of the enema dispenser 200 defines an interior chamber 208 configured (i.e., sized and shaped) to receive the bottle 206 therein and includes a shoulder stop 210 on a front end thereof. The piston 204 of the enema dispenser 200 comprises a piston head 212 and a piston rod 214. A proximal end 226 of the piston rod 214 is connected to the first crank 140 of the crankshaft 132 by the connecting rod 136.

Figure 19:
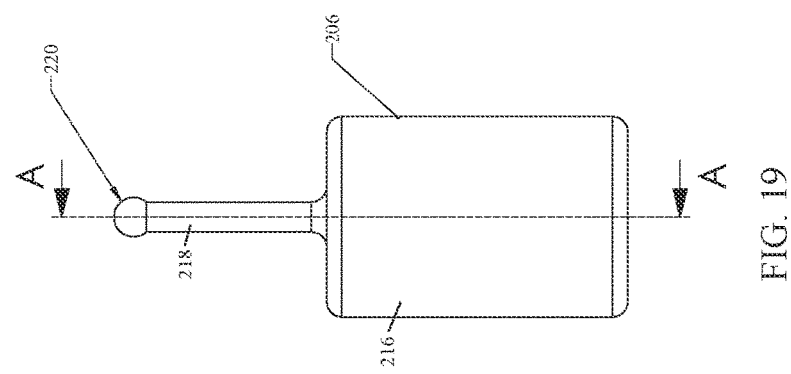
FIGS. 18 and 19 illustrate the bottle of the enema dispenser shown in FIGS. 14 and 15.
Figure 18:
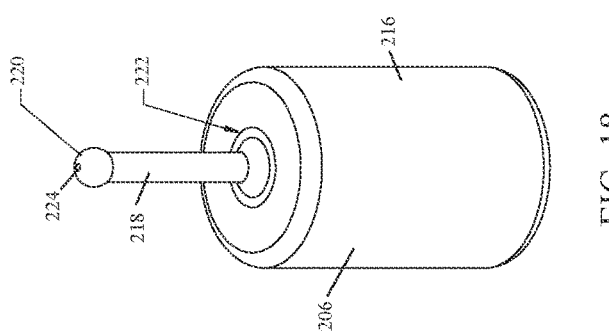
Figure 20:
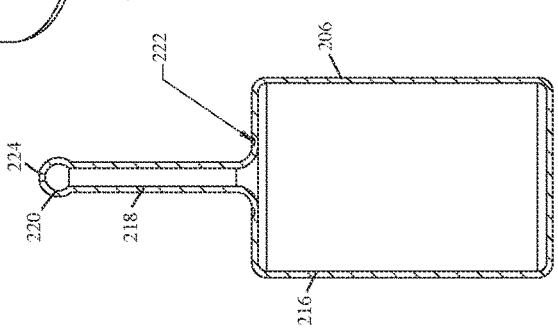
FIG. 20 illustrates a cutaway view of the bottle taken along line A-A shown in FIG. 19.

As shown best in FIGS. 18-20, the bottle 206 is made of a flexible material and comprises a body 216 and a nozzle 218, the nozzle 218 including a spherical insertion tip 220. The spherical insertion tip 220 is larger in diameter than the rest of the nozzle 218 and eases insertion of the nozzle 218 into a body cavity, such as the rectum. However, in some implementations, the spherical insertion tip 220 may have the same diameter as the rest of the nozzle 218. The spherical insertion tip 220 includes an exit opening 224 for enema liquid being expelled from the bottle 206. The bottle 206 also includes an annular groove 222 that extends about the junction between the body 216 and the nozzle 218. This annular groove 222 weakens the area of the bottle 216 located about the nozzle 218. In this way, the nozzle 218 can bend to the side before a force sufficient to cause the insertion tip 220 to damage or break the skin is applied during use of the enema dispenser 200.

As shown best in FIGS. 14 and 16, the shoulder stop 210 of the bottle holder 202 includes an opening 228 therein from which the nozzle 218 of the bottle 206 extends.

As shown in FIGS. 14-17, the head 212 of the piston 204 is slidably disposed within the interior chamber 208 of the bottle holder 202. In this way, when the piston rod 214 is acted on (or biased) by the connecting rod 136 of a modified suppository applicator 100, the piston head 212 slides upward to compress the bottle 206 against the shoulder stop 210 of the bottle holder 202 and thereby expels enema liquid from the exit opening 224 of the bottle 206.

Although not shown in the drawings, it should be understood that the example suppository applicator 100 disclosed herein could be used in conjunction with one or more implementations of the commode chair disclosed in non-provisional patent application Ser. No. 17/581,420, filed on Jan. 21, 2022, which is expressly incorporated by reference as if fully set forth herein. Specifically, one or more implementations of the suppository applicator 100 could be used in place of a digital stimulation device disclosed in nonprovisional patent application Ser. No. 17/581,420.

Reference throughout this specification to "an embodiment" or "implementation" or words of similar import means that a particular described feature, structure, or characteristic is included in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations are depicted in the drawings in a particular order, this should not be understood as requiring that such operations be performed in the particular order shown or in sequential order, or that all illustrated operations be performed, to achieve desirable results.

The invention claimed is:

1. A suppository applicator configured for use in depositing a suppository product in a body cavity, the suppository applicator comprising:
   a handle connected to a tool head by an elongate shaft; and
   a disposable applicator removably attached to the tool head;
   wherein:
   the disposable applicator is configured to contain the suppository product;
   the disposable applicator comprises a barrel member and a piston, the barrel member includes a longitudinal bore, and the piston is slidably disposed within the longitudinal bore adjacent the suppository product;
   the disposable applicator further comprises a guard positioned along a length of and perpendicular to the barrel member, the guard is configured to prevent the barrel member from being over-inserted into the body cavity; and
   the suppository applicator is configured such that rotation of the handle causes the suppository product to be expelled from the disposable applicator.

2. The suppository applicator of claim 1, further comprising a driving mechanism configured to expel the suppository product from the disposable applicator when the handle is rotated.

3. The suppository applicator of claim 2, wherein the driving mechanism comprises a crankshaft having a crank on each end, a drive pin positioned within the tool head, and a connecting rod operably connecting the crank on one end of the crankshaft to the drive pin.

4. The suppository applicator of claim 2, wherein the driving mechanism comprises a crankshaft that includes a crank on each end, a drive pin positioned within the tool head, and a connecting rod; the crankshaft extends through a longitudinally extending opening of the elongate shaft into an internal cavity defined by the tool head; the crank on a first end of the crankshaft extends through a slot in the elongate handle and is operably connected to the handle; the crank on a second end of the crankshaft is located within the cavity of the tool head and operably connected to the drive pin by the connecting rod.

5. The suppository applicator of claim 1, further comprising a suppository tool used to attach the disposable applicator to the tool head and remove the disposable applicator from the tool head, the suppository tool comprises an elongate body having an opening in each end, the opening in each end is configured to receive a distal section of the disposable applicator, one of the openings includes a barb positioned to catch on the distal section of the disposable applicator.

6. A suppository applicator configured for use in depositing a suppository product in a body cavity, the suppository applicator comprising:
- a handle connected to a tool head by an elongate shaft;
- a disposable applicator removably attached to the tool head, the disposable applicator is configured to contain the suppository product; and
- a driving mechanism configured to expel the suppository product from the disposable applicator when actuated.

7. The suppository applicator of claim 6, wherein the driving mechanism comprises a crankshaft having a crank on each end, a drive pin positioned within the tool head, and a connecting rod operably connecting the crank on one end of the crankshaft to the drive pin.

8. The suppository applicator of claim 6, wherein the driving mechanism comprises a crankshaft that includes a crank on each end, a drive pin positioned within the tool head, and a connecting rod; the crankshaft extends through a longitudinally extending opening of the elongate shaft into an internal cavity defined by the tool head; the crank on a first end of the crankshaft extends through a slot in the elongate handle and is operably connected to the handle; the crank on a second end of the crankshaft is located within the cavity of the tool head and operably connected to the drive pin by the connecting rod.

9. The suppository applicator of claim 8, wherein the handle is configured to rotate and thereby actuate the driving mechanism.

10. The suppository applicator of claim 6, wherein the disposable applicator comprises a barrel member and a piston, the barrel member includes a longitudinal bore, the piston is slidably disposed in the longitudinal bore adjacent the suppository product.

11. The suppository applicator of claim 10, wherein the disposable applicator further comprises a guard positioned along the length of and perpendicular to the barrel member, the guard is configured to prevent the barrel member from being over-inserted into the body cavity.

12. The suppository applicator of claim 6, further comprising a suppository tool used to attach the disposable applicator to the tool head and remove the disposable applicator from the tool head, the suppository tool comprises an elongate body having an opening in each end, the opening in each end is configured to receive a distal section of the disposable applicator, one of the openings includes a barb positioned to catch on the distal section of the disposable applicator.

13. An enema comprising:
- a handle connected to a tool head by an elongate shaft, the tool head includes an enema dispenser comprising a bottle holder, a piston, and a bottle configured to contain an enema liquid; and
- a driving mechanism configured to cause the piston to compress the bottle of the enema dispenser when actuated.

14. The enema of claim 13, wherein the bottle is made of a flexible material and comprises a body and a nozzle attached to the body, the nozzle includes a spherical insertion tip and a distal opening.

15. The enema of claim 14, wherein the bottle includes an annular groove that extends about a junction between the body and the nozzle.

16. The enema of claim 13, wherein the driving mechanism comprises a crankshaft having a crank on each end and a connecting rod operably connecting the crank on one end of the crankshaft to the piston of the enema dispenser.

17. The enema of claim 13, wherein the driving mechanism comprises a crankshaft that includes a crank on each end and a connecting rod; the crankshaft extends through a longitudinally extending opening of the elongate shaft into an internal cavity defined by the tool head; the crank on a first end of the crankshaft extends through a slot in the elongate handle and is operably connected to the handle; the crank on a second end of the crankshaft is located within the cavity of the tool head and operably connected to the piston by the connecting rod.

18. The enema of claim 17, wherein the handle is configured to rotate and thereby actuate the driving mechanism.

* * * * *